United States Patent [19]

Harsányi et al.

[11] Patent Number: 4,814,329

[45] Date of Patent: Mar. 21, 1989

[54] ANTIHYPERLIPOPROTEINEMIC 5-SUBSTITUTED SULFUR-CONTAINING BENZIMIDAZOLE DERIVATIVES

[75] Inventors: Kálmán Harsányi; Andrea Maderspach; András Jávor; György Hajós; György Fekete; Lázló Szporny; Péter Tétényi; Katalin Csomor; Egon Kárpáti; Béla Hegedüs; Márta Kápolnás née Pap; Márta Szöllösy; Anna Kállay née Sohonyai, all of Budapest, Hungary

[73] Assignee: Richter Gedeon Vegyeszeti Gyar R.T., Budapest, Hungary

[21] Appl. No.: 840,424

[22] Filed: Mar. 17, 1986

[30] Foreign Application Priority Data

Mar. 11, 1985 [HU] Hungary .................. 892/85

[51] Int. Cl.⁴ .................. A61K 31/55; C07D 417/12; C07D 413/12
[52] U.S. Cl. .................. 514/211; 514/224.5; 514/234.5; 514/322; 514/366; 514/387; 514/395; 540/544; 540/548; 544/34; 544/139; 546/199; 548/151; 548/305; 548/324; 548/327; 548/329
[58] Field of Search ............... 548/305, 324, 337, 151, 548/327, 329; 540/544, 548; 544/34, 139; 514/211, 226, 232, 322, 366, 387, 395, 234.5, 224.5; 546/199

[56] References Cited

U.S. PATENT DOCUMENTS 3,932,395   1/1976   Hideg et al. .................. 548/305

FOREIGN PATENT DOCUMENTS 0111993   6/1984   European Pat. Off. ............ 548/324

OTHER PUBLICATIONS

The Condensed Chemical Dictionary, 10th ed., 1981, p. 1017.

Primary Examiner—Richard A. Schwartz
Attorney, Agent, or Firm—Herbert Dubno; Jonathan Myers

[57] ABSTRACT

The invention relates to novel, sulfur-containing 5-substituted benzimidazole derivatives of formula I

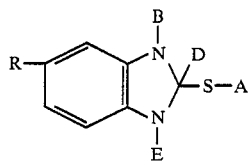

and acid-addition salts thereof antihyperlipoproteinemic action, a process for preparing the same, pharmaceutical formulations comprising the novel compound as active ingredient and a method for inhibiting atherosclerosis, trombus formation and treating hyperlipoproteinemic diseases.

30 Claims, No Drawings

ANTIHYPERLIPOPROTEINEMIC 5-SUBSTITUTED SULFUR-CONTAINING BENZIMIDAZOLE DERIVATIVES

TECHNICAL FIELD

The present invention relates to novel 5-substituted sulfur-containing benzimidazole derivatives of formula I

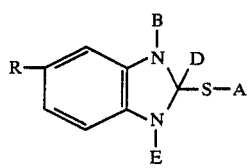

and the acid addition salts thereof, a process for preparing the same. An other object of the invention is a pharmaceutical formulation comprising the compounds of the formula I and the acid addition salts thereof useful against hyperlipoproteinemia. A further object of the invention is a method for treating hyperlipoproteinemia with the compounds of the invention.

In formula I

R stands for alkyl having 1 to 4 carbon atoms, phenyl-(alkyl having 1 to 4 carbon atoms), benzoyl or phenylsulfinyl group and D together with substituent A, B or E represents a further bond between a carbon atom and a heteroatom A is alkenyl or alkinyl having 3 or 4 carbon atoms, oxo-group or propyl substituted by one or more carbalkoxy having 2 to 5 carbon atoms, or alkyl substituted by a group of the formula $-NR^1R^2$, wherein $R^1$ and $R^2$ independently from each other represent hydrogen or alkyl having 1 to 4 carbon atoms, or $R^1$ and $R^2$ together represent an $\alpha,\omega$-alkylene chain having 4 or 5 carbon atoms optionally interrupted by oxygen, if R stands for alkyl having 1 to 4 carbon atoms, A is the same as defined hereinabove, further it can represent alkyl having 1 to 4 carbon atoms substituted by one or more halogen atoms, $-NR^1R^2$ groups, wherein $R^1$ and $R^2$ are the same as defined hereinabove, oxo, carboxy, hydroxy, hydroxyimino, phenyl, halogen phenyl, carbalkoxy having 2 to 5 carbon atoms, carbamoyl or nitrile groups, the substituents attaching to the other parts of the molecule through a hetero atom are attached to a carbon atom other than that attached to the sulfur atom, if R represents a group being different from alkyl having 1 to 4 carbon atoms, one of B and E together with D represents a further bond between a carbon atom and a hetero atom, and then the other is hydrogen or together with A represents an $\alpha,\omega$-alkylene chain having 2 to 3 carbon atoms; or B and E stand independently of each other for hydrogen or alkyl having 4 to 6 carbon atoms substituted by an oxo or hydroxyimino group $\delta$-position, but one of them must be different from hydrogen.

The scope of the present invention also covers the antihyperlipoproteinemic pharmaceutical compositions comprising an effective amount of the compounds of formula I or the acid addition salts thereof useful agaist atherosclerosis and thrombus formation.

For treating atherosclerosis only some drugs have been found and the effectiveness of these drugs is not unanimously acceptable. The limited importance of the therapeutic agents is demonstrated by the fact that the progress and occurrence of the pathological change can be suppressed by suitably choosen nutrition. The first representative of these agents was Clofibrate [2-(4-chlorophenoxy)isobutyric ethyl ester], and the structural elements of this compound appeared in the drugs put onto the market later.

BACKGROUND ART

In the prior art several articles refer to the preparation of benzimidazoline-2-thiol derivatives substituted on the sulfur atom. (J. Chem. Soc., 3311–3315. (1949); J. Pharm. Soc. Japan, 74, 1365.-9. (1954), CA: 49, 15876b; Yakugaku Zasshi, 78, 1378.-82 (1958). CA: 53, 8124h; Nauch Doklady Vysshei Shkoly, Khim.i Khim.Tekhnol., 333–337 (1959), CA: 54, 510b; Japaness Patent Application No. 10978(61), CA: 58, 13964h). Thiazino(3,2-a)benzimidazole is described by Current Sci. (India), 32, 454.-5. (1963), CA 59,15275h and Dopov Akad. Nauk RSR Ser. B. 801. (1975), while Japanese Kokai No. 50/52065 and CA 83 206268r relates to the preparation of succinic acid derivatives substituted by benzimidazol-2-yl-thio substituents in position 2.

Though the above articles refer to the possibility of the synthesis, they do not contain any reference to the medical use of the noval compounds of formula I.

DETAILED DESCRIPTION OF THE INVENTION

According to the invention the novel 5-substituted benzimidazole derivatives of the formula I are prepared by the following manners.

(a) For the preparation of the compounds of the formula I wherein E stands for hydrogen, B and D together form a further carbon-nitrogen bond and R and A are the same as defined hereinabove, a 5-substituted benzimidazoline-2-thione of the formula II

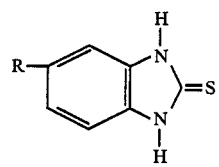

wherein R is the same as defines hereinabove as reacted with a compound of formula III

X-A          III wherein X stands for halogen, mesyloxy or tosyloxy group, A is the same as defined hereinabove, or (b) for the preparation of the compounds of formula I, wherein E is hydrogen, B and D together form a further carbon-nitrogen bond, R is the same as defined hereinabove and A represents ethyl substituted by carbalkoxy having 2 to 5 carbon atoms, a 5-substituted benzimidaziline-thione of formula II wherein R is the same as defined hereinabove is reacted with an acrylic acid derivative of formula IV $H_2C=CH-A^1$          IV (wherein $A^1$ stands for carboalkoxy having 2 to 5 carbon atoms) in acidic medium, or (c) for the preparation of 5-substituted benzimidazole derivatives of formula I, wherein E stands for hydrogen, B and D together form a further carbon-nitrogen bond, R is the same as defined hereinabove and A represents alkyl having 3 or 4 carbon atoms substituted by hydroxy on the second carbon atom calculated from the sulfur atom, a 5-substituted benzimidazoline-2-thione of formula II, wherein R is the same as defined hereinabove, is reacted with an oxirane derivative of formula V

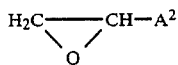

(wherein $A^2$ stands for methyl or ethyl) in basic medium, or (d) for the preparation of 5-substituted benzimidazoline-2-thione derivatives fo formula I, wherein B stands for hydrogen, R is the same as defined hereinabove, A and D represent a further carbon-carbon bond and E stands for alkyl having 4 to 6 carbon atoms substituted by an oxo group, a 5-substituted benzimidazoline-2-thione of formula II, wherein R is the same as defined hereinabove, is reacted with a vinylalkyl ketone derivative of formula VI,

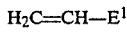

(wherein $E^1$ stands for alkyl having 2 to 4 carbon atoms substituted by an oxo group in position 1) in the presence of a trace amount of a catalyst or without catalyst, or (e) for the preparation of 5-substituted benzimidazole-2-thione derivatives of formula I, wherein B and E represents a $C_{4-6}$-alkyl group substituted by an oxo group, R is the same as defined above, and D and A represent a further carbon-carbon bond, a 5-substituted benzimidazoline-2-thione of formula II, wherein R is the same as defined hereinabove, is reacted with a vinylalkyl ketone of formula VI (wherein $E^1$ is the same as defined hereinabove), in the presence of a quaternery ammonium base, or (f) for the preparation of 5-position benzimidazole derivatives of formula I, wherein E stands for hydrogen, R is the same as defined hereinabove, B and D represent a further carbon-nitrogen bond, A stands for 1,2-dicarboxylethyl group, a 5-substituted benzimidazoline-2-thione of formula II, wherein R is the same as defined hereinabove, is reacted with maleinic anhydride, thereafter the mixture of the condensation products of formulae VII and VIII

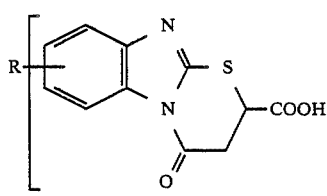

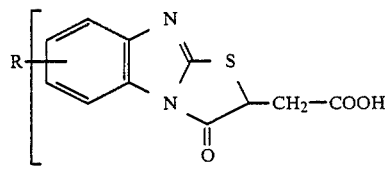

is hydrolized in acidic medium, or (g) for the preparation of 5-substituted benzimidazole derivatives of formula I, wherein B and D together form a further carbon-nitrogen bond, A and E together represent an α,ω-alkylene chain having 2 or 3 carbon atoms, a 5-substituted benzimidazoline-2-thione of formula II, wherein R is the same as defined hereinabove, is reacted with an α,ω-dihalogen-alkane of formula IX

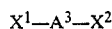

(wherein $X^1$ and $X^2$ stand for halogen, $A^3$ is an α,ω-alkylene chain having 2 or 3 carbon atoms) in the presence of acid-binding agents, and if desired the 5-substituted benzimidazole derivatives of the formula I thus obtained (in the formula I R, A, B, E and D are the same as defined above) are transformed into an other compound of formula I by esterification, imidation, salt formation or treating the compound obtained in the form of a salt with a base.

The 5-substituted benzimidazoline-2-thione derivatives of formula II used as starting m terials can be prepared in a manner known per se by reacting a suitable 4-substituted-1,2-diaminobenzene derivative with an alkaline metal xanhogenate (e.g. Org. Synth. Coll., Vol. 4, 569 (1963). The other reagents used in the procedures are well known, commercially available compounds.

Process variant (a) is preferably carried out in an organic solvent, e.g. in an alkanol having 1 to 4 carbon atoms between room temperature and 150° C. For binding the acid liberated the reaction different acid-binding agents, e.g. alkaline hydroxides, alkaline alcoholates, alkaline carbonates or alkaline bikarbonates can be used. It is preferred to bind the acid with the compound of the formula I instead of a supplementary acid-binding agent. Thus the compounds of formula O are obtained in the form of an acid addition salt, the free base is liberated with the aid of a base and it is extracted with a water non-miscible organic solvent from the aqeous solution. Preferably 0.1 to 2N aqeous solution of an alkaline hydroxide can be used as a base. As water non-miscible organic solvent preferably chlorinated hydrocarbons, e.g. dichloromethane or chloroform can be used. It was surprising that inconsistent with the teaching of the prior art (J. Heterocycl. Chem. 17, 1255 (1980), a cyclization side-process acconpanied with dehydratation did not occur when the 5-substituted benzimidazoline-2-thions of formula II and 4-halogen-acetoacetic ester were reacted according to the invention, only the S-alkylation reaction took place accompanied with the formation of hydrogen halogenide.

All of process variants (b), (d), (e) and (f) are alkylation by a reagent having a carbon-carbon bouble bond suitably activated from the point of view of nucleophilic addition. As such suitably activated reagents comprising a carbon-carbon double bond, acrylic acid derivatives (esters, amides and nitrile) of the formula IV in process variant (b), vinylalkyl ketones of formula VI in process variant (d) and maleic anhydride in process variant (f) can be used. If an above acid-derivative is used as a compound comprising a carbon-carbon double bond, then the sulfur atom will be substituted, while when vinylalkyl ketones are applied, then one or both nitrogen atom of the 5-substituted benzimidazoline-2-thione derivative of formula II will be alkylated depending on the reaction conditions. When maleinic anhydride is used, S-alkylation takes places at the first stage, but subsequently the 5-substituted-2-benzimidazolyl-2-thio-succinic anhydride acylates one of the nitrogen atoms being in the ring. Thus two products can be obtained in the respect of both the substituent being in position 5, both the two carboxy groups. The four tricyclic products have the formulae VII and VIII.

The great square brackets refer to the fact that as a result that substituent R may be attached to different carbon atoms of the ring, a mixture of isomers is obtained. However, it has no importance from the point of view of the preparation of the desired endproducts of formula I, as the same endproduct can be obtained by hydrolizing the four compounds.

From the knowledge of the prior art (Ukr. Khim. Zs., 41, 759 (1975); CA 83, 147426) it could not be expected that the vinyl alkyl ketone will alkylate the nitrogen atom(s). The single or double alkylation depends on the fact, whether the reaction is carried out without a catalyst or in the presence of a trace amount of a catalyst according to process variant (d) or in the presence of a quaternary ammonium base according to process variant (e). In the former case single, while in the latter case double alkylation takes place. As a quaternary ammonium base preferably from example benzyl-trimethyl-ammonium hydroxide (Triton B) can be used.

According to process variant (c) the alkylation is carried out with the aid of an oxirane derivative of formula V in a basic medium. According to a preferred embodiment of the process the 5-substituted benzimidazoline-2-thion derivative of formula II is first reacted with e.g. an alcoholate as a substance assuring the basic medium, then the anionic compound is reacted with the corresponding oxirane derivative of the formula V. The alcoholate is preferably used in equimolar amount.

A further embodiment of the alkylation is demonstrated by process variant (g). According to this process an α,ω-dihalogen alkane having 2 or 3 carbon atoms is used for alkylation. Both the sulfur and nitrogen atoms are alkylated and thus a tricyclic compound of formula I is obtained. The reaction is carried out similarly to process variant (a) with the difference that in the second stage at least one equivalent amount of a base is needed for the alkylation of the nitrogen atom.

The compounds of formula O prepared according to the processes of the invention can be transformed into other compounds of formula I in a manner known per se. Thus e.g. the compounds comprising oxo group(s) may be reacted with hydroxyl amine, and an oxime derivative comprising hydroxyimino group can be prepared. Reacting the compounds comprising hydroxy group with halogenating agents, halogenated derivatives, saponifying the compounds comprising esterified carboxy groups, compounds comprising free carboxy group, treating the compounds being in the form of a salt, free bases, while treating the latter compounds with acid, salts can be obtained. The compounds of formula I comprising free carboxy group can be transformed into salts by treating with a base.

For the preparation of the salts, all acids and bases can be used which ease either the separation, purification or the medical use of the target compounds. Thus for the formation of the salts, organic and inorganic acids and bases can be applied, e.g. hydrogen halogenids, e.g. hydrochloric acid, inorganic oxyacids (e.g., sulfuric acid, phosphoric acid), organic acids (acetic acid, citric acid, malic acid, succinic acid, methanesulfonic acid), the inorganic bases, e.g. sodium hydroxide and potassium hydroxide, potassium hydroxide, -carbonate, -bicarbonate, the organic bases, e.g. dicyclohexyl-amine and similar compounds.

Pharmaceutical compositions comprising the novel sulfur-containing 5-substituted-benzimidazole derivatives or the pharmaceutically acceptable salts thereof as active ingredient can be formulated by using diluents, filling, stabilizing agents, optionally osmosis pressure, pH adjusting, taste and smell influencing excipients, solvents, surface active agents, and other excipients. These formulations may be in liquid or semi-liquid state. As the representatives of the solid formulations the tablets, dragees, pills, powders and capsules can be mentioned. The liquid formulations can be e.g. drinkable or injectable compositions (solutions suspensions, emulsions). The cremes, ointments and gels can be mentioned as the representatives of the semi-liquid formulations.

The pharmaceutical compositions can preferably be formulated into such dosage forms (tablets, dragee, capsule, injection ampoulle, etc.), which comprise the whole amount of the active ingredient to be administered in a single dose, or the multiple or half, third, quarter amount of the same.

The dosage administered varies depending upon more factors, such as the age, health and weight of the recipient, nature and extent of the symptoms, frequency of the treatment. Usually a daily dosage of the active ingredient can be about 1 to 1000 mg/kg given in divided doses more times a day. The doses administered, the route of administration, frequency of administration is determined by the physician on the basis of his practice.

The chemical structure of the 5-substituted benzimidazole derivatives of formula I being useful against hyperlipoproteinemia is very different from the compounds used in this medical field. Therefore the application of the 5-substituted benzimidazole derivatives of the formula I is absolutely novel in this medical field. In the table comprising the pharmacological data Clofibrate is used as comparative compound, in order to illustrate the activity of the compounds of the invention, though its chemical structure is very far from the compounds of the invention.

The code numbers belonging to the compounds prepared according to the working examples are shown by the following table:

| code no. | working example | code no. | working example |
|---|---|---|---|
| 0200058 | 31 | 0200086 | 33 |
| 0200131 | 34 | 0200427 | 29 |
| 0202002 | 26 | 0202154 | 22 (hydrobromide) |
| 0202367 | 19 | 0202377 | 18 |
| 0202479 | 22 (hydrochloride) | 0202647 | 13 |
| 0203232 | 36 | | |

Atherosclerosis is a slowly progradiating process which is primarily characterized by the increasing of the plasma lipid components, e.g. cholesterol esters in the vein wall lesions. The process is induced by the injury of the endother layer of the vein wall. To the site of the injury the blood platelets adhere, different biologically active substances liberate from the platelets, which induce the multiplication of the muscle cells of the vein wall. Due to the injury, the normal barrier function of the vein wall ceases and the flowing of the plasma ingredients, e.g. lipoproteins, cholesterol esters together with the active agents derived from the platelets into the lower layers of the vein walls starts (Arteriosclerosis, 1, 229 to 311 (1981).

The low density atherogenic lipoproteins (LDL) and the high density lipoproteins (HDL) having protective activity according the epidemioligic data, carrying the main portion of cholesterol from the lipoproteins are of great importance. (Lancet, 1, 16–19 (1975))

As a summary, it can be stated that on the one hand thrombogenic, on the other hand lipid or lipoprotein components take part in the process. Therefore it was also a target of search to find such compounds which preferably influence the level of the lipoproteins, i.e. decrease the amount of the atherogenic LDL and increase the cholesterol content of the protective HDL, simultaneously exhibit a significant antiaggregation action.

Whistar hannover male rats weighing 140–160 g were fed for 7 days with a rat fodder supplemented with 1.5% of cholesterol, 0.5% of sodium cholate and 5% of solid fat. (Schurr, P. E.; Schultz, J. R., Day, D. E.; Atherosclerosis Drug Discovery Ed.: C. E. Day, Plenum, New York 215 (1976) and Acta Pharm. Hung., 49, 182. (1979) During this time the total cholesterol level of the serum increased with 200–250% compared to the normal level, while the amount of the HDL chloesterol diminished by 45–50%. Groups consisting of six animals were formed. The compounds of the invention were administered orally starting on the fourth day of the addition of the cholesterol fodder and it was continued by the end of the experiments, by the seventh day, in one or two doses. Then after a 18 hour starving the animals were bled to death under etheric narcosis on the 8th day. The blood samples were centrifuged and the serum total cholesterol and the HDL cholesterol were determined by Backmann enzymatic test, while the triglyceride concentration of the serum was determined by Van Handel's method (J. Lab.: Clin. Med. 41, 486 (1953). The amount of the LDL+VLDL was measured by manganese precipitation turbidimetrically (Schurr, P. E., Schulz, J. R., Day, C. E.: Atherosclerosis Drug Discovery Ed.: C. E. Day, Plenum Press, New York 215 (1976). The antiaggreagtion activity was measured in vitro on human plasm being rich in thrombocytes by a Chrono-log aggregometer. The aggregation was induced by ADP, adrenaline, collagen and arachidonic acid. The determination of the inhibition of the lipidperoxidation was carried out by thiobarbituric acidic method with the aid of washed human thrombocyte suspension. The lipidperoxidation was induced by N-ethyl-alenicimide (Arzneimittel-Forschung 29, 981 (1979).

The results of the in vivo experiments are summarized in Table 1 and 2.

More of the novel 5-substituted benzimidazole-derivatives of formula I were found to have a preferable influence on the lipoprotein composition of the blood serum of the rats fed with cholesterol. This fact was demonstrated by the diminishing of the lipid content of the serum and the increasing of the level of the protective HDL.

TABLE 1

| Code of the compound | Dose mg/kg p.o. | serum cholesterol change | serum triglyceride change | LDL + VLDL % change | HDL cholesterol % change |
|---|---|---|---|---|---|
| 0200058 | 30.0 | −14.0 | +1.0 | −19.4 | +30.0 |
|  | 100.0 | −10.6 | +12.8 | −9.4 | +44.9 |
| 0200086 | 30.0 | −26.0 | −24.9 | −22.1 | −35.0 |
|  | 100.0 | −35.4 | −27.2 | −24.8 | +19.4 |
| 0200131 | 30.0 | −17.4 | −18.8 | −17.5 | +10.0 |
|  | 100.0 | −16.9 | −25.4 | −5.9 | +57.0 |
| 0200060 | 30.0 | −13.2 | −28.5 | −4.3 | −43.9 |
|  | 100.0 | −27.8 | +8.1 | −16.1 | −43.9 |
| 0200427 | 30.0 | −45.5 | −63.5 | −58.2 | −17.7 |
|  | 100.0 | −51.7 | −67.2 | −54.4 | −12.1 |
| 0202002 | 30.0 | −22.0 | +27.8 | −.38 | −16.9 |
|  | 100.0 | −68.0 | −29.4 | −55.8 | −16.9 |
| 0202054 | 30.0 | −34.5 | −30.0 | −38.1 | +27.0 |
|  | 100.0 | −49.3 | −25.3 | −57.5 | +71.3 |
| 0202377 | 30.0 | −36.5 | +58.0 | +1.0 | −13.5 |
|  | 100.0 | −52.4 | +115.7 | −14.5 | +61.2 |
| 0302367 | 30.0 | −37.4 | −19.0 | −45.2 | +47.1 |
|  | 100.0 | −42.6 | −16.1 | −50.7 | +26.0 |
| 0203232 | 30.0 | −32.1 | +29.3 | −27.6 | +6.8 |
|  | 100.0 | −48.6 | −18.3 | −45.9 | +6.8 |
| 0202647 |  |  |  |  |  |
| Clofibrate | 100.0 | −24.7 | −20.0 | −11.2 | −20.0 |

TABLE 2

The affect of compound no. 0202479 to the rats with the cholesterol diet in 10 day treatments

| No. of the compound | Dose mg/kg p.o. | Serum cholesterol | Serum triglyceride | LDL + VLDL percentile | HDL cholesterol change |
|---|---|---|---|---|---|
| 0202479 | 10.0 | −7.8 | −3.1 | −20.8 | +47.7* |
|  | 30.0 | −41.5* | −47.7** | −48.5** | +40.1 |
|  | 100.0 | −66.3 | −55.8** | −80.5** | +56.1** |
| Clofibrate | 100.0 | −23.0 | −24.5 | −37.9 | −7.4 |

* 0.01 P 0.05;
** P 0.01

Such compound was e.g. compound No. 0200058 (see Table 1) which caused 45% increase of HDL and a smaller decrease of the level of the total cholesterol of the serum administerek in a dose of 100 mg/kg. Compound No. 0200131 had similar activity. More remarkable changes could be observed when the compound No. 0202377 was used in a dose of 100 mg/kg as it resulted in the 52.4 percentile decrease of the total cholesterol level of the serum, while the HDL-cholesterol content increased with 61.2%. The LDV+VLDL level decreased is smaller extent. Compound No. 0202647 exhibited especially excellent activity is a dose of 100 mg/kg as it resulted in the 34.5 percentile decrease of the total serum cholesterol level. 41.5 percentile decrease of the LDL+VLDL level of HDL with 49%. Especially great serum lipid decreasing activity was exerted by compound No. 0200427 administered in a dose of 100 mg/kg, which decreased with 51.7% the total serum cholesterol, 67.2% of the serum triglyceride and 54.4% of the LDL+VLDL level. The compound also decreased the HDL level, though in smaller extent. The compound No. 0202154 was also very effective in a dose of 100 mg/kg. It decreased the level of the total cholesterol with 49.3%, the level of the triglyceride with 25.3%, while the amount of LDL+VLDL with 57.5%. The level of the HDL cholesterol increased with 71.3%.

Compound No. 0202479, the hydrochloride salt of the above compound was also remarkably effective. The results obtained by using this compound are summarized in Table 2 and 3.

TABLE 3

| Concentration µM | Aggreagetion inhibition | | | Arachidonic acid |
|---|---|---|---|---|
| | ADP | Adrenaline | Collagene | |
| 250 | 20 | 9 | 6 | 100 |
| 500 | 59 | 16 | 16 | — |
| 1000 | 66 | 73 | 39 | — |

The antiaggreagetion activity data of Clofibrate are as follows (medium inhibitory concentration µM) (Biochem. Pharmacol. 30. 14, 2013 (1981))

ADP: 100 µM
Adrenaline: 700 µM
Collagene: 1700 µM
Arachidonic acid: 5000 µM

Table 3 illustrated the platelet aggregation inhibiting activity of the compound. The aggregation caused by ADP and adrenaline was inhibited by the compound—similarly to Clofibrate—in the second phase this effect could be observed in lower doses in the case of compound No. 0202479 then in the case of Clofibrate. The aggregation induced by arachinodic acid was inhibited with 100% by the compound used in a concentration of 250 µM, while Clofibrate was ineffective. These results refer to the fact that the compound inhibits the biosyntheses of prostaglandine in the thrombocytes through the route of cyclooxygenase. The result were affirmed by the inhibition of the lipideperoxidation, the medium inhibiting concentration was 24 µM in this experiment.

The acute toxicity of this compound was examined on male and female mice and rats by oral administration. The animals were observed for 14 days. The acute $LD_{50}$ valve was 960 mg/kg in the case of mice, while it was over 2000 mg/kg in the case of rats.

Summerizing the test results it can be stated that the 5-substituted benzimidazole derivatives of formula I represent a novel type of compound which on the one hand preferably influences the pathogenic lipoprotein level, diminishes the concentration of the atherogenic lipoproteins and increases the amount of the protective HDL cholesterol important from the point of view of heart attack. Besides these properties it also inhibits platelet aggregation and lipideperoxidation. Its activity surpasses in every respect the activity of Clofibrate used as reference compound.

The invention is illustrated by the following, non-limiting examples.

The IR spectras given in the working examples were taken by using potassium bromide on a spectrophotometer of Perkin-Elmer 257 type. The site of the absorption maximus are given in vawe number (cm$^{-1}$), referring always to group to which they belong. The accuracy of the date given is ±5-8 cm$^{-1}$.

The magnetic resonance spectras (NMR) were taken at a frequency of 60 MHz in a Varian EN-360 equipment. The solvent or solvent mixture used is given in parenthesis after the sign "NMR"m thereafter the values are given in ppm.

DMSO$_{d6}$=dentero-dimethyl-sulfoxide

EXAMPLE 1

2-(2-(1-piperidyl)-ethylthio)-5-methyl-benzimidazoledihydrochloride 4.87 g (30 mmoles) of 5-methyl-benzimidazoline-2-thione, 6.54 g (35.5 mmoles) of 2-(1-piperidyl)-ethylchloride hydrochloride, 2.78 g (33 mmoles) of sodium hydrogencarbonate are dissolvent in 60 ml of methanol and the mixture is refluxed for 6 hours. The inorganic salt is filtered off, the filtrate is evaporated, and the title compound is precipitated by adding ethyl acetate and hydrochloric ethyl acetate. Weight: 9.32 g (90%). Melting point: 229°–230° C., which does not change after recrystallization from ethanol.

Elemental analysis ($C_{15}H_{23}Cl_2N_3S$) (M=348.33); calculated, %: N, 12.06; S, 9.21; Cl, 20.36. found, %: N, 12.31; S, 9.11; Cl, 20.51.

Spectroscopic data:
IR (KBr): $\nu$=3600–3300 (OH+N+H) 3150–2100 (N+H) 1610 (C=N) 795 (aromatic H def.) cm$^{-1}$.

NMR (D$_2$O): δ=2,0 b (C—CH$_2$/$_3$C), 3.8 m (N+—CH$_2$), 2.5 s (Ar—CH$_3$) 7,4 m (Ar—H) 3,1 b (S—CH$_2$) ppm

EXAMPLE 2

5-methyl-2-2-(2,3,5,6-tetrahydro-1,4-oxazine-4-yl)-ethylthio-benzimidazole dihydrochloride 4.11 g (25 mmoles) of 5-methyl-benzimidazoline-2-thione, 5.58 g (30 moles) of N-2-chloroethyl-morpholine-hydrochloride and 2.55 g (30.3 mmoles) of sodium hydrogencarbonate are refluxed in ethanol for 6 hours, then the reaction mixture is evaporated off. 1.1 g of sodium hydroxide dissolved in 10 ml of water, then 20 ml of dichloromethane are added, the phases are separated and the extraction is repeated twice. The combined dichloromethane solution is concentrated, then the salt is formed by the addition of hydrochloric ethyl acetate. 8.28 g (94.5%) of title product are obtained, which can be crystallized from ethanol. M.p.: 250°–251° C.

Elemental analysis ($C_{14}H_{21}Cl_2N_3OS$) (M=350.31): Calculated % C, 48.00; H, 6.04; N, 12.00; S, 9.15. Found % C, 48.25; H, 6.17; N, 12.28; S, 9.11.

Spectroscopic data:
IR (KBr): $\nu$3200–2100 (N+—N), 1610 (C=N), 1080 (C—O—C).

NMR (D$_2$O): δ2.5 s (Ar—CH$_3$), 3.5–4.2 m (CH$_2$—k), 7.4 m (Ar—H) ppm.

EXAMPLE 3

2-3-Aminopropylthio-5-benzyl-benzimidazole-dihydrochloride 6 g (25 mmoles) of 5-benzyl-benzimidazoline-2-thione, 3.9 g (30 mmoles) of 3-chloropropylamine hydrochloride and 2.55 g (30.3 mmoles) of sodium hydrogencarbonate are reacted as described in Example 2. After the inorganic salt is filtered off, the starting benzimidazole-thione (2.85 g) crystallizes from the ethanolic solution. To the substance obtained by concentration of the filtrate aqueous sodium hydroxide solution and dichloromethane are added according to the method described in Example 2. After repeated extraction the dichloromethane phases are concentrated and the title dihydrochloride salt is precipitated by the addition of hydrochloric isopropanol. The melting point of the endproduct is 212°–216° C.

Spectroscopic data:
IR (KBr) $\nu=3200-2100$ (N—H), 1610 (C=N), 1595 (aromatic skeleton) 778, 730, 695 (aromatic H def.) cm$^{-1}$.

NMR (CDCl$_3$+DMSO$_{d6}$): $\delta=2.2$ t (C—CH$_2$—C), 3.1 b (S—CH$_2$), 3.8 t (N—CH$_2$), 4.1 s (Ar—CH$_2$—Ar), 7.2-7.6 m (Ar—H) 8.4 b$^x$ (NH) ppm.

EXAMPLE 4

5-Benzyl-2-(2-(1-piperidyl)-ethylthio)-benzimidazole and the dihydrochloride salt thereof 6 g (25 mmoles) of 5-benzyl-benzimidazoline-2-thione, 5.52 g (30 mmoles) of 2-(1-piperidyl)-ethylchloride hydrochloride and 2.55 g (30.3 mmoles) of sodium hydrogen-carbonate are reacted as described in example 2. The reaction mixture is concentrated, the residue is extracted with aqueous sodium hydroxide solution and dichloromethane according to Example 2. The dichloromethane phases are concentrated, 30 ml of ethylacetate are added to the residue. The precipitated 5-benzyl-2-2-(1.piperidyl)-ethylthio-benzimidazole base (4.6 g; 52.3%) is filtered off and recrystallized from acetonitrile. M.p.: 107° C.

Elemental analysis (C$_{21}$H$_{25}$N$_3$S) (M: 351.49): Calculated % N, 11.95; S, 9.12. Found % N, 12.16; S, 9.64. The dihydrochloride salt is prepared by hydrochloric isopropanol.

M.p.: 228°-230° C.

Elemental analysis (C$_{21}$H$_{27}$Cl$_2$N$_3$S) (M.: 424,42): Calculated % C, 59.42; H, 6.41; Cl, 16.7; N, 9.9; S 7.55. Found % C, 59.62; H, 6.10; Cl, 16.43; N, 9.75; S 7.18.

Spectroscopic data:
IR (KBr) $\nu=3200-2300$ (N—H$^+$), 1610 (C=N) 1592 (aromatic skeleton 1270 (S—CH$_2$), 2770 (N—CH$_2$), 778, 736, 700 (aromatic H.def./cm$^{-1}$.

NMR (CDCl$_3$): $\delta=1.7$ b (C—(CH$_2$)$_3$-C), 2.5-3.5 m (S—CH$_2$, N—CH$_2$), 4.1 s (Ar—CH$_2$—Ar), 6.8-7.4 m (Ar—H) ppm.

EXAMPLE 5

5-Benzyl-2-(2-(2,3,5,6-tetrahydro-1,4-oxazine-4-yl)-ethylthio)-benzimidazole and the dihydrochloride salt thereof 6 g (25 mmoles) of 5-benzyl-benzimidazoline-2-thione, 5.58 g (30 mmoles) of 2-chloroethyl-morpholine hydrochloride and 2.55 g of sodium hydrogencarbonate are reacted in 40 ml of ethanol at boiling temperature for 5 hours. After filtering off the inorganic salt and concentration of the mixture, the residue is treated with 30 ml of ethylacetate. The benzimidazole base thus obtained (7.31 g) (m.p.: 150° C.) is filtered off.

Elemental analysis (C$_{20}$H$_{23}$N$_3$OS) (M.: 353.46): Calculated % C, 67.95; H, 6.55; N, 11.88; S, 9.07. Found % C, 67.71; H, 6.9; N, 12.06; S, 8.97.

Spectroscopic data:
IR (KBr): $\nu=3200-2300$ (N—H), 1610 (C=N), 1110 (C—O—C) 1592 (aromatic skeleton), 2800 (N—CH$_2$), 1270 (S—CH$_2$), 795, 740, 704 (aromatic H def.) cm$^{-1}$.

NMR (CDCl$_3$): $\delta=2.6-2.8$ m, (N—CH$_2$), 3.2 m (S—CH$_2$), 3.8 m (O—CH$_2$), 4.0 s (CH$_2$—Ar), 6.8-7.4 m (Ar—H) ppm.

The melting point of the dihydrochloride salt of the base is 224°-225° C. It can be recrystallized from n-butanol.

Elemental analysis (C$_{20}$H$_{25}$Cl$_2$N$_3$OS) (M: 426.38): Calculated % C, 56.33; H, 5.91; Cl, 16.63. Found % C, 56.79; H, 6.1; Cl, 15.98.

EXAMPLE 6

2-(2-diisopropylamino-ethylthio)-5-benzyl-benzimidazole phosphate 6 g (25 mmoles) of 5-benzyl-benzimidaziline-2-thione, 6 g (30 mmoles) of 2-(diisopropylamino)-ethylchloride hydrochloride and 2.55 g of sodium hydrogencarbonate are boiled in 40 ml of ethanol for 5 hours. The inorganic salt is filtered off, the filtrated is evaporated according to the method described is Example 2. After the addition of aqueous sodium hydroxide solution the filtrate is extracted with dichloromethane, the dichloromethane phase is concentrated and the title salt is precipitated with the aid of ethanolic phosphoric acid solution for the residue. The product recrystallized from 95% ethanol melts at 194°-195° C., and proved to be uniform when it was chromatographed using methanol as eluent.

Spectroscopic data:
IR (KBr): $\nu=3700-2000$ (N$^+$—H+ O—H), 1615 (C=N), 1085 (PO$_4$), 1595 (aromatic skeleton) 797, 732, 700 (aromatic H def.) cm$^{-1}$.

NMR (CDCl$_3$+DMSO$_{d6}$): $\delta=1.4$ d (C—CH$_3$), 3.5 b (S—CH$_2$, N—CH, 4.0 s (Ar—CH$_2$—Ar), 6.8-7.4 m (Ar—H) ppm.

EXAMPLE 7

2-(2-diethylamino-ethylthio)-5-benzyl-benzimidazole dihydrochloride 6 g (25 mmoles) of 5-benzyl-benzimidazoline-2-thione, 5.16 g (30 mmoles) of 2-(diethylamino)-ethylchloride hydrochloride and 2.55 g of sodium hydrogencarbonate are reacted in 40 ml of ethanol. After filtering off the inorganic salt and concentration of the solution, the title product is precipitated by hydrochloric ethanol.

M.p.: 152°-154° C. Weight: 6.85 g (66.44%).

Elemental analysis: (C$_{20}$H$_{27}$Cl$_2$N$_3$S) (M: 412.41): Calculated %: C, 58.24; H, 6.6; N, 10.18. Found %: C, 57.97; H, 6.28; N, 10.3.

Spectroscopic data:
IR (KBr): $\nu3100-2100$ (N$^+$—H), 1610 (C=N), 1592 (aromatic skeleton), 793, 734, 700 (aromatic H def.) cm$^{-1}$.

NMR (CDCl$_3$) $\delta1.5$ t (CH—CH$_3$), 3.4 qa (CH$_3$—CH$_2$), 3.8 b (S—CH$_2$), 4.2 b (N—CH$_2$), 4.0 s (Ar—CH$_2$—Ar), 7.2-7.7 m (Ar—H) ppm.

EXAMPLE 8

Phenyl-(2-(2-propenylthio)-benzimidazole-5-yl)-methanone hydrochloride 6.55 g (25.76 mmoles) of 5-benzoyl-benzimidazol-2-thione, 2.45 ml of allyl chloride and 40 ml of ethanol are refluxed for 20 hours, thereafter further 2.45 ml of allyl chloride are added and the mixture is refluxed for further 5 hours. The product precipitates upon cooling. The weight (86.7%). M.p.: 182°-183° C. (after recrystallization from isopropanol)

Elemental analysis (C$_{17}$H$_{15}$ClN$_2$OS) (M: 330.82): Calculated %: C, 61.71; H 4.57; Cl$^-$ 10.71; S, 9.69. Found %: C, 61.53; H 4.57; Cl$^-$ 10.7; S, 9.87.

Spectroscopic data:
IR (KBr): $\nu3200-2000$ (N$^+$—H), 1652 (C=O), 1622 (C=C), 1590 (aromatic skeleton), 828, 750, 690 aromatic H def.) cm$^{-1}$.

NMR (CDCl$_3$): $\delta=4.4$ d (S—CH$_2$), 5.2-6.3 m (vinyl group) 7.3-8.3 m (Ar—H), 13.5 b$^x$ (NH) ppm.

EXAMPLE 9

5-Phenylsulfinyl-2-(2-propenylthio)-benzimidazole hydrochloride 6.86 g (25 mmoles) of 5-phenylsulfinyl-benzimidazoline-2-thione and 4.9 ml (60 mmoles) of allylchloride are refluxed in 50 ml of ethanol for 24 hours. Then the reaction mixture is concentrated and the residue is crystallized from acetonitrile. The weight of the filtered endproduct is 7.68 g (87.55%). After recrystallization from ethanol it melts at 168° C.

Elemental analysis ($C_{16}H_{15}ClN_2OS_2$) (M: 350.88): Calculated % C, 54.76; H, 4.3; S, 18.27. Found % C, 54.52; H, 4.18; S, 18.01.

Spectroscopic data:

IR (KBr): $\gamma = 3100-2000$ (N$^+$—H), 1630 (C=C), 1183 (S=O), 1600 (aromatic skeleton), 816, 750, 690 (aromatic H def.) cm$^{-1}$.

NMR (DMSO$_{d6}$) $\delta = 4.2$ d (S—CH$_2$), 5.0–5.6 m (x CH$_2$), 5.6–6.2 m (x CH), 7.5–8.2 m (Ar—H) ppm.

EXAMPLE 10

2-(2-Diisopropylamino-ethylthio)-5-methyl-benzimidazole 6.16 g (37.5 mmoles) of 5-methyl-benzimidazoline-2-thione, 9 g (45 mmoles) of 2-(diisopropylamino)-ethylchloride hydrochloride and 3.52 g (41.9 mmoles) of sodium hydrogencarbonate are refluxed in 60 ml of ethanol for 6 hours. After the filtration of the salt and concentration of the filtrate the residue is extracted with dichloromethane and aqueous sodium hydroxide solution as described in Example 2. The aqueous phase is further extracted with dichloromethane, the combined organic phases are concentrated, the residue is recrystallized from 47 ml of ethylacetate. The title product thus obtained weights 6.65 g (61%) and melts at 109°–110° C.

Elemental analysis ($C_{16}H_{25}N_3S$) (M: 291.45): Calculated %: C, 65.93; H, 8.65; N, 14.42; S, 11.00. Found %: C, 65.73; H, 8.26; N, 14.43; S, 10.75.

Spectroscopic data:

IR (KBr): $\nu = 3300-2100$ (N—H), 1618 (C=N), 1599, 1580 aromatic skeleton), 800 Ar def.) cm$^{-1}$.

NMR (CDCl$_3$): $\delta = 1.1$ d (CH—CH$_3$) 2.4 s (Ar—CH$_3$), ~3.1 m (CH, CH$_2$—k), 6.8–7.4 m (Ar—H) ppm.

EXAMPLE 11

2-(2-dimethylamino-ethylthio)-5-benzyl-benzimidazole dihydrochloride

According to the method described in Example 2 g (25 mmoles) of 5-benzyl-benzimidazoline-2-thione, 4.32 g (30 mmoles) of 2-(dimethylamino)-ethylchloride hydrochloride and 2.55 g of sodium hydrogencarbonate are refluxed in methanol. The salt is filtered off, the filtrate is concentrated and treated with aqueous sodium hydroxide solution and dichloromethane. The organic phase is separated, concentrated and the salt is precipitated by adding hydrochloric ether. 8.15 g (84.8%) of 2-(2-dimethylaminoethylthio)-5-benzyl-benzimidazole dihydrochloride are obtained, which melts at 204° C. after recrystallization from isopropanol.

Elemental analysis ($C_{18}H_{23}Cl_2N_3S$) (M 384.36) Calculated % Cl$^-$, 18.45; N, 10.93; S, 8.34. Found % Cl$^-$, 18.27; N, 11.07; S, 8.12. Spectroscopic data: IR (KBr): $\nu = 3200-2000$ (N—H), 1613 (C=N), 1596 (aromatic skeleton), 1448 (N—CH$_3$ def.), 795, 732, 698 (aromatic H def.) cm$^{-1}$. NMR (D$_2$O): $\delta = 3.3$ s (N—CH$_3$), 3.5–4.1 m (N—CH$_2$, S—CH$_2$, 4.2 s (Ar—CH$_2$—Ar), 7.3–7.7 m (Ar—H) ppm.

The free base is obtained as a crystalline substance if the residue obtained after the concentration of the above dichloromethane solution is recrystallized from acetonitrile. The 2-(2-dimethyl-amino-ethylthio)-5-benzylbenzimidazole melts at 100° C.

EXAMPLE 12

5-Methyl-2-(2-propinylthio)-benzimidazole 4.11 g 5-methyl-benhimidazoline-2-thione, 2.3 ml of propargyl bromide are refluxed in 40 ml of ethanol for 2 hours. During the boiling the hydrobromide salt of the product precipitates. The reaction mixture is concentrated, then worked up according to the method of Example 2. After working up the dichloromethane solution the residue is recrystallized from 160 ml of carbon tetrachloride. 4.24 g (84%) of title product are obtained which melts at a temperature of 125° C.

Elemental analysis ($C_{11}H_{10}N_2S$) (M.: 202.28): Calculated % C, 65.31; H, 4.98; N, 13.85; S, 15.85. Found % C, 65.12; H, 4.68; N, 13.75; S, 15.97.

Spectroscopic data:

IR (KBr): $\nu = 3200-2200$ (N—H), 3290 (C—H), 1618 (C=N), 1603 (aromatic skeleton), 797 (aromatic H def.) cm$^{-1}$.

NMR (CDCl$_3$) $\delta = 2.2$ t (C—H), 2.4 s (Ar—CH$_3$) 4.0 d (S—CH$_2$), 6.9–7.5 m (Ar—H), 9.8 s$^x$ (N—H) ppm.

EXAMPLE 13

5-Benzyl-2-(2-propinylthio)-benzimidazole 6 g (25 mmoles) of 5-benzyl-benzimidazoline-2-thione, 2.3 ml of propargyl bromide and 40 ml of ethanol are refluxed for 3 hours. The reaction mixture is concentrated, the crystalline substance thus obtained is worked up according to the method of Example 2. The dichloromethane extract is concentrated and the residue is crystallized from 20 ml of toluene. 4.53 g (65.2%) of title product are obtained melting at a temperature of 109° C.

Elemental analysis ($C_{17}H_{14}N_2S$) (M.: 278.37) Calculated % C, 73.34; H, 5.07; N, 10.07; S, 11.52. Found % C, 73.21; H, 5.40; N, 9.92; S, 11.72.

Spectroskopic data:

IR (KBr): $\nu = 3200-2200$ (N—H), 3270 (C—H), 2120, (C C), 1613 (C=N) 1593 (aromatic skeleton), 790, 725, 695 (arometic H def.) cm$^{-1}$.

NMR (CDCl$_3$): $\delta = 2.2$ t (C—H), 3.9 d (S—CH$_2$), 4.0 s (Ar—CH$_2$—Ar), 7.2 s (C$_6$H$_5$-), 6.9–7.5 m Ar—H (3), 11.8 s$^x$ (N—H) ppm.

EXAMPLE 14

2-(2-Dimethylamino-ethylthio)-5-methyl-benzimidazole 4.11 g (25 mmoles) of 5-methyl-benzimidazoline-2-thione, 4.32 g (30 mmoles) of 2-(dimethylamino)-ethylchloride hydrochloride and 2.55 g of sodium hydrogencarbonate are refluxed in 50 ml of ethanol for 6 hours. The reaction mixture is filtered off, concentrated and the residue is worked up according to the method of Example 2. The dichloromethane extracts are concentrated and the residue is crystallized from petrolether. 3.81 g of 2-(2-dimethylamino-ethylthio)-5-methyl-benzimidazole are obtained, which melting point does not change after recrystallizaton from acetonitrile. M.p.: 103° C.

Elemental analysis (C$_{12}$H$_{17}$N$_3$S) (M.: 235.35): Calculated % C, 61.24; H, 7.28; N, 17.85; S, 13.63. Found % C, 61.15; H, 7.06; N, 17.74; S, 13.43.

Spectroscopic data:

IR (KBr): $\nu$=3300–2200 (N—H), 1435 (N—CH$_3$ def.), 1600 (aromatic skeleton), 1618 (C=N), 800 (Ar—H def.) cm$^{-1}$.

NMR (CDCl$_3$): δ=2.4 s (N—CH$_3$), 2.5 s (Ar—CH$_3$), 2,8 m (S—CH$_2$), 3,2 m (N—CH$_2$) 6.8–7.5 m (Ar—H), 12 b$^x$ (N—H) ppm.

EXAMPLE 15

5-Methyl-2-(2-propenylthio)-benzimidazole 4.11 g (25 mmoles) of 5-methyl-benzimidazoline-2-thione and 2.45 ml of allyl chloride are refluxed in ethanol, then the reaction mixture is evaporated. The residue is worked up according to the method described in Example 2. The residue obtained after the dichloromethane extraction is recrystallized from 7 ml acetonitrile. 3.29 g (64.66%) of 5-methyl-2-(2-propenylthio)benzimidazole melting at a temperature of 128° C. are obtained.

Elemental analysis (C$_{11}$H$_{12}$N$_2$S) M.: 204.3): Calculated % C, 64.66 H, 5.92 N, 13.72. Found % C, 64.27 H, 5.95 N, 13.91.

Spectroscopic data:

IR(KBr): $\nu$=3200–2200 (N—H), 1620 (C=C+C=N), 982, 920 (—CH=CH), 1580 (aromatic skeleton), 800 (aromatic H def.) cm$^{-1}$.

NMR (CDCl$_3$+DMSO$_{d6}$) δ=2.5 s (Ar—CH$_3$), 3.9 d (S—CH$_2$), ~5.2 m (=CH$_2$), ~6 m (—CH), 6.9–7.5 m (Ar—H), 11.7 b$^x$ (N—H) ppm.

EXAMPLE 16

5-benzyl-2-(2-methylthio)-benzimidazole 6 g (25 mmoles) of 5 benzyl-benzimidazoline-2-thione and 1.88 ml of methyl iodide are refluxed in 50 ml of ethanol. The reaction mixture is evaporated and the residue is worked up according to the method described in Example 2. The combined organic phases are evaporated and the residue crystallized from acetonitrile. 5.23 g (82.36%) of title product are obtained which melts at a temperature of 139° C.

Elemental analysis (C$_{15}$H$_{14}$N$_2$S) (M.: 254.35): Calculated % C, 70.82; H, 5.53; N, 11.02. Found % C, 70.50; H, 5.61; N, 11.05.

Spectroscopic data:

IR (KBr): $\nu$=3200–2200 (N—H), 1620 (C=N), 1600 (aromatic skeleton), 820, 734, 700 (aromatic H def.) cm$^{-1}$.

NMR (CDCl$_3$): δ=2.7 s (S—CH$_3$), 4.1 s (Ar—CH$_2$—Ar), 7.3 s (C$_6$H$_5$—), 7.0–7.6 m (Ar—H (3 ), 10,5 b$^x$ (N—H) ppm.

EXAMPLE 17

5-Benzyl-2-(2-hydroxy-1-propylthio)-benzimidazole 4.8 (20 mmoles) of 5-benzyl-benzimidazoline-2-thione and 0.46 g sodium dissolved in ethyl alcohol and 2 ml of 1,2-propylenoxide are refluxed for 5 hours. The reaction mixture is evaporated and 50 ml of benzene and 20 ml of 1N sodium hydroxide solution are added. The aqueous phase is extracted twice with 10 ml of benzene, the combined benzene phases are evaporated and the residue is crystallized from nitromethane. The title product thus obtained melts at a temperature of 115° C.

Elemental analysis (C$_{17}$H$_{18}$N$_2$OS) (M.: 298.4): Calculated % C, 68.42; H, 6.08; N, 9.39. Found % C, 68.36; H, 5.80; N, 9.14.

Spectrocopic data:

IR (KBr): $\nu$=3300–2200 (N—H+O—), 1627 (C=N), 1602, 1580 (aromatic skeleton), 822, 738, 700 (aromatic H def.), 1280 (S—CH$_2$def.) cm$^{-1}$.

NMR (CDCl$_3$+CMSO$_{d6}$): δ=1.4 d (C—CH$_3$), 3.3 t (S—CH$_2$), 4.0 s (Ar—CH$_2$-Ar), 4.2 m (—CH—), 6.8–7.2 m (Ar—H), 8 b$^x$ (O—H+N—H) ppm.

EXAMPLE 18

5-Benzyl-2-(2-hydroxyethylthio)-benzimidazole 5.75 g (24 mmoles) of 5-benzyl-benzimidazoline-2-thione, a solution of 1 g of sodium hydroxide and 8 ml of water, 2 ml (30 mmoles) of 2-chloroethanol and 30 ml of ethanol are refluxed for an hour. The reaction mixture is evaporated and extracted with water and dichloromethane, then the aqueous phase is extracted with dichloromethane. The residue of the combined organic phases is solidified under ether. After filtration and crystallization from ethyl acetate 4.63 g (68.1%) of title product are obtained. M.p.: 108°–109° C.

Elemental analysis (C$_{16}$H$_{16}$N$_2$OS) (M.: 284.38): Calculated % N, 9.85. Found % N, 9.72.

Spectroscopic data:

IR (KBr): $\nu$=3300–2100 (N—H, O—H), 1622 (C=N), 1227 (S—CH$_2$ def.) 1600, 1582 (aromatic skeleton), 777, 731, 698 (aromatic H def.) cm$^{-1}$ NMR (DMSO$_{d6}$) δ=3.4 t (S—CH$_2$), 3.8 t (O—CH$_2$), 3.2–4.0 b$^x$ (O—H+N—H), 4,1 s (r-CH$_2$Ar), 6.9–7.6 m (Ar—H (3), 7.4 s (C$_6$H$_5$—)

EXAMPLE 19

5-Benzyl-2-(3-hydroxypropylthio)-benzimidazole 12.02 g (50 mmoles) of 5-benzyl-benzimidazoline-2-thione, 4.72 ml of 3-chloro-1-propanol, 2.0 g (50 mmoles) of sodium hydroxide dissolved in water and ethanol are reacted as described in the above Example. The recovering of the product is carried out similarly. 9.76 g (65.4%) of title product are obtained. M.p.: 103°–105° C.

Elemental analysis (C$_{17}$H$_{18}$N$_2$OS) (M.: 298.4): Calculated % N, 9.39; S, 10.75. Found % N, 9.61; S, 10.52.

Spectroscopic data:

IR (Kbr): $\nu$=3300–2000 (O—H,N—H), 1626 (C=N), 1270 (S—CH$_2$) 1603, 1582 (aromatic skeleton), 803, 785, 740, 700 (aromatic H def.) cm$^{-1}$.

NMR (CDCl$_3$): δ=1.9 m (C—CH$_2$—), 3.5 t (S—CH$_2$), 3.8 t (O—CH$_2$), 4.1 s (Ar—CH$_2$Ar), 7.8–7.5 m (Ar—H (3), 7.3 s (C$_6$H$_5$—) 8.4 s$^x$ (O—H+N—H).

EXAMPLE 20

3,4-Dihydro-8-benzyl-2H-1,3-thiazino(3,2-a)benzimidazole 12.02 g (50 mmoles) of 5-benzimidazoline-2-thione, 5.32 ml (60 mmoles) of 1-bromo-3-chloropropane and 2 g of sodium hydroxide dissolved in 6 ml of water are boiled in ethanol. As the pH of the mixture turns to acidic (bromothimoleblue), further 4.2 g of sodium hydrogencarbonate (50 mmoles) are added as acid-binding agent. About 3 hours are needed for the transformation of the whole starting benzimidazole. The inorganic salt is filtered off, the filtrate is evaporated. The residue is treated with an 1:1 mixture of ethanol and ethyl acetate, the separated salt is filtered again and the filtrate is concentrated. The crystalline residue is taken up with ethyl acetate and filtered. The crude title product weighing 14.2 g is recrystallized from butanol. 12.8 g of pure title product are obtained. Yield: 92% M.P.: 145°-147° C.

Elemental analysis ($C_{17}H_{16}N_2S$) (M.: 280.41): Calculated % C, 72.81; H, 5.75; N, 9.99. Found % C, 73.18; H, 5.34; N, 10.45.

Spectroscopic data:

IR (KBr): $\nu = 1620$ (C=N), 1265 (S—$CH_2$ def.), 1602, 1580 (aromatic skeleton) 795, 750, 702 (Ar—H def.) $cm^{-1}$.

NMR ($CDCl_3$): $\delta = 2.5$ m (C—$CH_2$—C), 3.2 t (S—$CH_2$), 4.1 m (N—$CH_2$), 4.2 s (Ar—$CH_2$), 6.9-7.5 m (Ar—H) ppm.

EXAMPLE 21

2-Butylthio-5-benzimidazole-hydrobromide 12.02 g (50 mmoles) of 5-phenyl-benzimidazoline-2-thione, 6.3 ml of butyl bromide are boiled in ethanol until the starting benzimidazole derivative disappears. Then the solvent is evaporated off and the title product obtained as a residue is crystallized from a mixture of ethanol and ether. 14.56 g (77.2%) of title product melting at a temperature of 144°-145° C. are obtained.

Elemental analysis ($C_{18}H_{21}BrN_2S$) (M.: 3.77): Calculated % C, 57.29 H, 5.62 N, 7.42. Found % C, 57.25 H, 5.64 N, 7.27. Spectroscopic data:

IR (KBr): $\nu = 3200$-2200 ($N^+$—H), 1618 (C=N), 1603 (aromatic skeleton), 796, 732, 698 (Ar—H def.) $cm^{-1}$.

NMR ($CDCl_3$) $\delta = 0.9$ t (C—$CH_3$), 1.6 b (C—$CH_2$—C), 3.6 t (S—$CH_2$), 4.1 s (Ar—$CH_2$—Ar), 7.2-7.9 m (Ar—H), 13 $b^x$ (N—H) ppm.

EXAMPLE 22

5-Benzyl-2-(2-propenylthio)-benzimidazole hydrobromide, hydrochloride and base 12 g (50 mmoles) of 5-benzyl-benzimidazoline-2-thione and 4.5 ml (60 mmoles) of allyl bromide are boiled until the starting benzimidazole compound disappears (1-2 hours). The solution is evaporated, 30 ml of ethyl acetate added then 30 ml of ethyl acetate is distilled off. Upon adding 30 ml of ethyl acetate the substance becomes crystalline. The weight of the crude product is 15.1 g (83.2%), which is recrystallized from butanol. The hydrobromide salt of the title product (13.5 g; 74.3%) melts at a temperature of 141°-142° C.

Elemental analysis ($C_{17}H_{17}BrN_2S$) (M.: 361.32): Calculated % C, 56.52; H, 4.75; N, 7.75; S 8.88. Found % C, 56.28; H, 4.62; N, 7.79; S 8.45.

Spectroscopic data:

IR (KBr): $\nu = 3350$ (N—H), 3200-2000 (N—H), 1620 (C=C+C=N), 1600, 1582 (aromatic skeleton), 928 (C—CH=$CH_2$), 785, 726, 700 (aromatic H def.) $cm^{-1}$.

NMR ($CDCl_3DMSO_{d6}$): $\delta = 4.1$ s (Ar—$CH_2$—Ar), 4.3 d (S—$CH_2$, 5,1-6.2 m (C—CH=$CH_2$), 7.2 s ($C_6H_5$—), 7.7 d (Ar—H (3), 11 $b^x$ (N—H) ppm.

The hydrochloride salt can be prepared in a similar way by using allyl chloride. M.p.: 120°-122° C.

The base is liberated preferably from the salt: 5.66 g (15 mmoles) of the above hydrobromide salt is shaken with 50 ml of dichloromethane and a solution of 0.62 g of sodium hydroxide and 15 ml of water. The phases are seaprated and the aqueous phase is extracted twice with 20 ml of dichloromethane. The distillation residue of the organic phase is crystallized from ethyl acetate. 3 g (71.5%) of title base melting at a temperature of 126°-127° C. are obtained.

Elemental analysis ($C_{17}H_{16}N_2S$) (M.: 280.39): Calculated % S, 11.43. Found % S, 11.18.

Spectroscopic data:

IR (KBr): $\nu = 3200$-2200 (N—H), 1630 (C=C+C=N), 1600, 1586 (aromatic skeleton), 800, 735, 700 (aromatic H def.) $cm^{-1}$.

NMR ($CDCl_3 + DMSO_{d6}$): $\delta = 3.9$ d (S—$CH_2$), 4.0 s (Ar—$CH_2$—Ar), 5.0-6.1 m (—CH=$CH_2$), 7.1 s ($C_6H_5$—), 6.8-7.4 m (Ar—H)(3) ppm.

EXAMPLE 23

5-benzyl-2-(2-chloroethylthio)-benzimidazole hydrochloride 12.1 g (40 mmoles) of 5-benzyl-2-(2-hydroxyethylthio)-benzimidazole are reacted with 5.15 ml of thionyl chloride in a mixture of 100 ml of benzene and 10 ml of acetonitrile. After teh evolution of the gas is ceased, the reaction mixture is evaporated, 30 ml of ethyl alcohol are added to the residue and the solution is evaporated off again. The product thus obtained is purified by chromatography. It is dissolved in ethyl acetate, introduced onto the colomn and thereafter eluted with ethyl acetate then ethanol. The target compound appears in the third fraction, its weight is 8.26 g. M.p.: 140°-145° C.

Elemental analysis ($C_{16}H_{16}Cl_2N_2S$) (M.: 339.28): Calculated % C, 56.64; H, 4.75; Cl 20.90. Found % C, 56.17; H, 4.58; Cl 21.07.

Spectroscopic data:

IR (KBr): $\nu = 3200$-2000 ($N^+$—H), 1620 (C=N), 1598, 1580 (aromatic skeleton), 790, 747, 704 (Ar—H def.) $cm^{-1}$.

NMR ($CDCl_3$) $\delta = 3.9$ t (S—$CH_2$+Cl—$CH_2$), 4.1 s (Ar—$CH_2$—Ar), 7,3 s ($C_6H_5$—) 7.0-7.9 (Ar—H (3) ppm.

EXAMPLE 24

S-(5-Benzyl-2-benzimidazolyl)-thioacetic acid ethyl ester 0.46 g (20 mmoles) of metal sodium are dissolved in 40 ml of ethanol. To the ethylate 4.8 g (20 mmoles) of 5-benzyl-benzimidazoline-2-thione are added and 2.4 ml of bromoacetic acid ethyl ester are added dropwise at room temperature. After 4 hours boiling the salt is filtered off, the mother liquor is evaporated and 60 ml of petrol-ether are added to the distillation residue. Thus 7.23 g of crude title product are isolated. This is purified by suspending in water. Thus 6.33 g (97.1%) of title compound melting at a temperature of 103° C. are obtained, which can be crystallized from methanol.

Elemental analysis ($C_{18}H_{18}N_2O_2S$) (m.: 325.41): Calculated % C, 66.23; H, 5.56; N, 8.58; S, 9.83. Found % C, 65.95; H, 5.34; N, 8.76; S, 9.65.

Spectroskopic data:

IR (KBr): $\nu = 3200$-2200 (N—H), 1727 (C=O), 1625 (C=N), 1200 (C—O—C), 1604, 1583 (aromatic skeleton), 826, 734, 697 (aromatic H def.) $cm^{-1}$.

NMR ($DMSO_{d6}$): $\delta = 1.1$ t (C—$CH_3$), 4.0 s (Ar—$CH_2$—Ar), 4.1 qa (O—$CH_2$), 4.2 s (S—$CH_2$), 7.0-7.4 m (Ar—H), 12 $b^x$ (N—H) ppm.

EXAMPLE 25

2-(5-benzyl-2-benzimidazolyl)thio)-1-(4-chlorophenyl)-ethanone 0.23 g (10 gatoms) sodium metal are dissolved in ethanol, then 2.4 g (10 mmole) of 5-benzyl-benzimidazoline-2-thione and 2.4 g of (10.2 mmoles) of 4-chlorophenacyl bromide are added to this solution. After 3 hour boiling the reaction product is filtered off from the cooled reaction mixture, then washed free of bromide with water. Thus 3.73 g of title compound melting at a temperature of 175° C. are obtained. It can be recrystlized from about 50 fold amount of methanol.

Elemental analysis ($C_{22}H_{17}ClN_2OS$) (M.: 392.91): Calculated % Cl, 9.02; N, 7.13; S, 8.16. Found % Cl, 8.76; N, 7.04; S, 7.93.

Spectroscopic data:

IR (KBr): $\nu$=3200–2200 (N—H), 1672 (C=O), 1090 (Ar—Cl), 1590 (aromatic skeleton), 823, 735, 700 (aromatic H def.) cm$^{-1}$.

NMR (CDCl$_3$+DMSO$_{d6}$): $\delta$=4.0 s (Ar—CH$_2$—Ar). 4.9 s (S—CH$_2$), 6.6 b$^x$ (N—H). 7.2 s (C$_6$H$_5$—) 7.7 m (Ar—H(7) ppm.

EXAMPLE 26

1-((5-benzyl-2-benzimidazolyl)thio)-2-propanone 0.46 g of sodium metal are dissolved in ethanol, then 2.4 g (10 mmoles) of 5-benzyl-benzimidazoline-2-thione are added to this solution under heating. Then 2.4 ml (30 mmoles) of chloroacetone are added dropwise. The reaction mixture is boiled for 1 hour, evaporated, then 40 ml benzene and 20 ml of aqueous 1N sodium hydroxide solution are added. The phases are separated, and the distillation residue of the benzene solution is crytalized with ether. Thereafter the title product thus obtained is recrystallized from isopropanol. M.p.: 102° C.

Elemental analysis (C$_{17}$H$_{16}$N$_2$OS) (M.: 296.38): Calculated % C, 68.88; H, 5.44; N, 9.45; S, 10.81. Found % C, 69.21; H, 5.42; N, 9.45; S, 11.18.

Mass spectra data:
Molecule ione: 296
Basic peak: 253
Main fragments: 281, 279, 278, 221, 180, 152, 91.

EXAMPLE 27

S-(5-Benzoyl-2-benzimidazolyl)-3-thiopropionic acid ethylester hydrochloride 12.7 g (50 mmoles) of 5-benzoyl-benzimidazoline-2-thione is stirred with 5.4 ml of ethyl acrylate (50 mmoles) an 10 ml of glacial acetic hydrochloric acid. After an impernament dissolution a high amount of precipitate separates. 17.59 g (90.2%) of title product are obtained which can be recrystallized from dioxane without changing of the melting point. M.p. 158°–159° C.

Elemental analysis (C$_{19}$H$_{19}$ClN$_2$O$_3$S) (M.: 390.89) Calculated %: C, 58.38; H, 4.90; N, 7.17; S 8.20 Cl$^-$, 9.07. Found %: C, 58.53; H, 4.83; N, 7.18; S 8.16 Cl$^-$, 9.5.

Spectroscopic data:

IR (KBr) $\nu$=1720 (ester C=O), 1645 (Ar C=O), 1615 (C=N), 1595 (aromatic skeleton), 1150 (C—O—C), 3200–2000 (N—H), 795, 749, 705 (aromatic H def.) cm$^{-1}$.

NMR (in Polysol) $\delta$=1.2 t (C—CH$_3$), 3.0 t (CO—CH$_2$—CH$_2$), 3.9 t (S—CH$_2$), 4–1 qa (O—CH$_2$), 7.2—8.3 m (aromatic H) 11 b$^x$ (N—H) ppm.

EXAMPLE 28

S-(5-Benzyl-2-benzimidazolyl)-3-thiopropionic acid ethyl ester hydrochloride 12 g (50 mmoles of 5-Benzyl-benzimidazoline-2-thione and 5.4 ml (50 mmoles) of ethyl acrylate are dissolved in a mixture of glacial acetic and hydrochloric acid, then the reaction mixture is stirred until the disaapearence of the starting benzimidazole derivative (for about 6 hours). Then the reaction mixture is evaporated, the residue is crystallized under ether, thus 17.44 g of title product are obtained. Yield: 92.5 g. M.p. 127°–128° C.

Elemental analysis (C$_{19}$H$_{21}$ClN$_2$O$_2$S) (M. 376.91): Calculated % C, 60.54; H, 5.62; Cl$^-$, 9.41; N, 7.43; S, 8.51. Found % C, 60.63; H, 5.60; Cl$^-$, 9.74; N, 7.72; S, 8.85.

Spectroscopic data:

IR (KBr); $\nu$=3200–2100 (N$^+$—H), 1720 (C=O), 1193 (C—O—C), 1617 (C=N), 1600 (aromatic sceleton), 783, 729, 698 (aromatic H def.) cm$^{-1}$.

NMR (CDCl$_3$) $\delta$=1.0 t (C—CH$_3$), 2.9 t (CO—CH$_2$), 3.9 t (S—CH$_2$), 4.0 s (Ar—CH$_2$Ar), 4.1 qa (O—CH$_2$), 7.2 s (C$_6$H$_5$—) 7.1–7.8 m (aromatic H (3)) ppm.

EXAMPLE 29

1-(5-Benzyl-2-thioxo-1-benzimidazolyl)-3-butanone 16 g (66.7 mmoles) of 5-benzyl-benzimidazoline-2-thione are stirred in 30 ml of methylvinylketone for 25 hours. The excess of the detone is distilled off under vacuum (0.1 to 0.2 bars), 50 ml of isopropanol are poured onto the residue, then the solvent is distilled off. Upon pouring ether onto the residue, crystalls are obtained. These are filtered off, and recrystallized from acetonitrile, then ethanol. The title product thus obtained melts at a temperature of 141°–142° C.

Elemental analysis (C$_{18}$H$_{18}$N$_2$OS) (M.: 310.41): Calculated % C, 69.64; H, 5.84; N, 9.03; S, 10.33. Found % C, 69.79; H, 6.05; N, 8.91; S, 10.08.

Spectroscopic data:

IR (KBr): $\nu$=3300–2300 (N—H), 1695 (C=O), 1627 (C=N), 1598 (aromatic skeleton), 788, 741, 694 (aromatic H def.) cm$^{-1}$.

NMR (CDCl$_3$+DMSO$_{d6}$): $\delta$=2.1 s (CO—CH$_3$), 2.9 t (CO—CH$_2$), 4.0 s (Ar—CH$_2$—Ar), 4.3 t (N—CH$_2$), 6.8–7.5 m (Ar—H) ppm.

EXAMPLE 30

(1,3-bis(3oxo-butyl)-2-thioxo-benzimidazole-5-yl)-phenylmethynone 12.7 g (50 mmoles) of 5-benzoyl-benzimidazoline-2-thione, 75 ml of methylvinylketone and 2 drops of 40%, methanolis Triton B solution (benzyl-trimethyl ammonium hydroxide, products of Röhm and Haas, Philadelphia, USA) are boiled for 2 hours. Upon cooling 12.7 g of title product crystallizes. This product melts at 126°–127° C. after recreastallization from methanol. From the original mother liquor further 2.2 g of crude product can be separated.

Elemental analysis (C$_{22}$H$_{22}$N$_2$O$_3$S) (M.: 394.49) Calculated % C, 66.98; H, 5.62; N, 7.10; S, 8.13. Found % C, 66.94; H, 5.64; N, 7.14; S, 7.95.

Spectroscopic data:

IR (KBr): $\nu$=1710 (aliphatic ketone), 1640 (aromatic ketone), 1597, 1575 (aromatic sceleton), 789, 750, 705 (aromatic H def.) cm$^{-1}$.

NMR (CDCl$_3$) δ=2.2 s (CO—CH$_3$) 3.1 t (CO—CH$_2$), 4.5 t (N—CH$_2$), 7.3-7.9 m (Ar—H) ppm.

EXAMPLE 31

1,3-bis(3-Oxo-butyl)-5-benzyl-2-thioxo-benzimidazole 14.4 g (60 mmoles) of 5-benzyl-benzimidazoline-2-thione amd 45 ml of methylvinylketone are boiled for 4 hours in the presence of 2 drops of 40%, methynolic Triton B solution. Then the reaction mixture is evaporated off. During storage the distillation residue crystallizes. This is recrystallized from 200 ml of ethanol and thus 19.86 g (87%) of title product melting at a temperature of 98°-100° C. are obtained.

Elemental analysis (C$_{22}$H$_{24}$,N$_2$O$_2$S) (M.: 380.5): Calculated % C, 69.44 H, 6.36 N, 7.36 S, 8.43. Found % C, 69.76 H, 6.68 N, 7.18 S, 8.54.

Spectroscopic data:

IR (KBr): ν=1704 (C=O), 1600 (aromatic skeleton), 798, 730, 701 (aromatic H def.) cm$^{-1}$.

NMR (CDCl$_3$+DMSO$_{d6}$): δ=2.1 s (CH$_3$—C=O), 3.1 t (CO—CH$_2$), 4.1 s (Ar—CH$_2$—Ar), 4.5 t (N—CH$_2$), 7.1-7.4 m (Ar—H) ppm.

EXAMPLE 32

1,3-bis(3-Hydroxyimino-butyl)-5-benzyl-2-thioxo-benzimidazole 3.8 (10 mmoles) of the product prepared according to Example 31 are boiled with 3.5 g of hydroxylamine hydrochloride for 2 hours in a mixture of 60 ml of ethanol and 30 ml fo water in the presence of 6.8 g of sodium acetate trihydrate. After cooling the title product is filtered off and crystallized from 50% ethanol just after washing with water. 3.73 g of pure title product melting at a temperature of 117°-119° C. are obtained.

Elemental analysis (C$_{22}$H$_{26}$SN$_4$O$_2$) (M.: 410.53): Calculated % C, 64.36; H, 6.38; N, 13.65; S, 7.82. Found % C, 64.10; H, 6.30; N, 13.48; S, 8.11.

Spectroscopic data:

IR (KBr): ν=3600-2200 (O—H), 1655 (C=N), 965 (C=S), 1600, 1585 (aromatic skeleton), 788, 728, 700 (aromatic H def.)cm$^{-1}$.

NMR (CDCl$_3$+DMSO$_{d6}$): δ=1.9 s (—CN—CH$_3$), 2.5-3.0 m (—CN—CH$_2$), 4.1 s (Ar—CH$_2$—Ar), 4.5 t (N—CH$_2$), 6.9-7.3 m (Ar—H), 10.1 b$^x$ (N=O—H) ppm.

EXAMPLE 33

S-(5-Benzoyl-2-benzimidazolyl)-2-thio-succinic acid 25.4 (100 mmoles) of 5-benzoyl-benzimidazoline-2-thione and 9.8 g of maleic anhydrid are boiled for 36 hours in 400 ml of dioxane. The reaction mixture is evaporated, the residue was taken onto a filter with ether. 31.41 g of product are obtained which comprises the corresponding 3-oxo-2H-thiazolol(3,2-a)benzimidazole-2-yl-acetic acids and 2,3-dihydro-4-oxo-thiazino(3,2-a)benzimidazole 2-yl carboxylic acids in about equimolar amount. 17.32 g of the above mixture is poured into a solution of 8 g of sodium hydroxide and 300 ml of water and stirred until dissolution at room temperature. Upon acdifying the mixture 15.62 g (85.8%) of S-(5-benzoyl-2-benzimidazolyl)-2-thio-succinic acid separates, which melts at a temperature of 195°-196° C. after recrystallization from 50% ehatnol.

Elemental analysis (C$_{18}$H$_{14}$N$_2$O$_5$S) (M.: 370.37): Calculated % C, 58.37 H, 3.81 S, 8.66. Found % C, 58.75 H, 3.74 S, 8.97.

Spectroscopic data

IR (KBr): ν=3400-2000 (O—H), 1690 (S=O acid), 1650 (C=O ketone), 1615 (C=N), 1595 (aromatic skeleton), 784, 753, 720 (Ar—H def.)cm$^{-1}$.

NMR (DMSO$_{d6}$) δ=3.0 d (—CH$_2$—), 4.8 t (—CH—), 7.4-7.8 m (Ar—H) ppm.

EXAMPLE 34

S-(5-Benzyl-2-benzimidazolyl)-2-thio-succinic acid 39.39 g (14 mmeles) of 5- benzyl-benzimidazoline-2-thione are dissolved in 300 ml of dioxane, thereafter 16.08 g (164 mmoles) of maleic anhydride are added and the solution is boiled for 42 hours. Dioxane is evaporated off and the residue is triturated with ether. 48.3 g of a mixture of the corresponding 3-oxo-2H-thiazolo(3,2.a)benzimidazole-2-yl acetic acids and 2,3-dihydro-4-oxo-thiazino(3,2-a) benzimidazole-2-yl-carboxylic acids in about equimolar amount. 19.99 g of the above mixture is left to stand in a solution of 9.4 g of sodium hydroxide and 200 ml of water. Upon acidification 17.25 g of title product separates, which is recrystallized from 750 ml of 50% ethanol.

M.p. 206°-208° C.

Elemental analysis (C$_{18}$H$_{16}$N$_2$O$_4$S) (M.: 356.4): Calculated % C, 60.66; H, 4.53; N, 7.86; S, 9.00. Found % C, 61.43; H, 5.23; N, 7.98; S, 9.23.

Spectroscopic data:

IR (KBr): ν=3700-2100 (O—H, N—H), 1725 (C=O), 1222 (C—OH), 1595 (Aromatic skeleton), 860, 799, 734, 702 (aromatic H def.) cm$^{-1}$.

NMR (CDCl$_3$+DMSO$_{d6}$): δ=2.8-3.1 m (CO—CH$_2$), 4.1 s (Ar—CH$_2$—Ar), 4.6 m (CO—CH—) 7.1-7.7 m (Ar—H), 8.0 b$^x$ (OH—NH) ppm.

EXAMPLE 35

4-[(5-Methyl-2-benzimidazolyl)thio]-acetic acid ethyl ester hydrochloride 4.92 g (30 mmoles) of 5-methyl-benzimidazoline-2-thione and 4.05 ml of 4-chloro-acetoaceticester are boiled in 50 ml of ethanol for 6 hours. The substance precipitated upon cooling is filtered off and recrystallized from 60 ml of acetonitrile. 3.83 g (39%) of title product melting at a temperature of 172° C. are obtained.

Elemental analysis (C$_{14}$H$_{17}$ClN$_2$O$_3$) (M.: 328.83): Calculated % Cl$^-$, 10.78; S, 9.75. Found % Cl$^-$, 10.92; S, 9.51.

Spectroscopic data:

IR (KBr): ν=3300-2200 (N$^+$—H), 1740 (C=O ester), 1717 (C=O ketone), 1625 (C=N), 1195 (C—O—C), 1585 (aromatic skeleton), 803 (aromatic H def.) cm$^{-1}$.

NMR (CDCl$_3$) δ=1,2 t (CH$_2$—CH$_3$), 2,4 s (Ar—CH$_3$), 3.5 b$^x$ (CO—CH$_2$—CO), 4.1 qa (O—CH$_2$), 4.7 b (S—CH$_2$). 6.9-7.5 m (Ar—H), 11.6 b$^x$ (N—H) ppm.

The base is liberated from the hydrochloride salt thus obtained is aqaeous solution by equivalent amount of sodium hydrogencarbonate. The melting point of the base is 97°-98° C. after recrystallization from carbon tetrachloride.

Elemental analysis (C$_{14}$H$_{16}$N$_2$O$_3$S ), (M.: 292.36): Calculated % C, 57.51; H, 5.52; N, 9.58. Found % C, 57.27; H, 5.36; N, 9.70.

Spectroscopic data:

IR (KBr): ν=3300-2200 (N—H), 1723 (C=O), 1170 (C—O—C), 1578 (aromatic skeleton), 802 (aromatic H def.) cm$^{-1}$.

Mass spectra data:
Molecule ione: 292
Basic peak: 177
Main fragments: 246, 218, 204, 163, 145

EXAMPLE 36

4-[(5-Benzyl-2-benzimidazolyl)thio]acetoacetic acid ethylester hydrochloride 7.2 g (30 mmoles) of 5-benzyl-benzimidazoline-2-thione and 4.05 ml of 4-chloro-acetoacetic ester are boiled in 50 ml of ethanol for 7 hours. The solution is put into the refrigerator and the crystals are filtered off. The crude title product weighing 7.61 g is recrystallized from 35 ml of isopropanol, thus 6.51 g (53.6%) pure product are obtained, which melts at a temperature of 150°–153° C.

Elemental analysis ($C_{20}H_{21}ClN_2O_3S$) (M.: 404.92): Calculated % C, 59.32; H, 5.23; N, 6.92; Cl$^-$, 8.76. Found % C, 59.65; H, 5.10; N 7.16; Cl$^-$, 8.64.

Spectroscopic data:
IR (KBr): $\nu$=3200-2200 (N—H), 1730 (C=O ester), 1710 (C=O ketone) 1625 (C=N), 1185 (C—O—C), 1592 (aromatic skeleton), 812, 720, 696 (Ar—H def.) cm$^{-1}$.

NMR (CDCl$_3$): $\delta$=1.1 t (CH$_2$CH$_3$), 3.5 b$^x$ (CO—CH$_2$—CO), 3.9 s (Ar—CH$_2$—Ar), 4.0 qa (O—CH$_2$) 4.8 b (S—CH$_2$), 6.9–7.5 m (Ar—H), 11 b$^x$ (N—H) ppm.

We claim:

1. A compound of Formula (Ib)

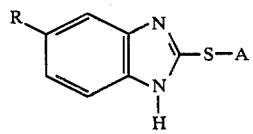

wherein
A is $C_1$ to $C_4$ alkyl substituted by $C_2$ to $C_5$ carboalkoxy; and
R is phenyl-($C_1$ to $C_4$ alkyl), benzoyl, or phenylsulfinyl; or a pharmaceutically acceptable acid addition salt thereof.

2. 5-benzyl-2-(2-carboethoxyethylthio)-benzimidazole or a pharmaceutically acceptable acid addition salt thereof as defined in claim 1.

3. A compound of Formula (Ic)

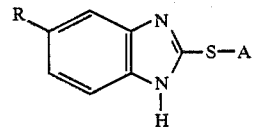

wherein
A is $C_2$ to $C_4$ alkyl substituted by hydroxy on the second carbon atom calculated from the sulfur atom; and
R is phenyl-($C_1$ to $C_4$ alkyl), benzoyl or phenylsulfinyl; or a pharmaceutically acceptable acid addition salt thereof.

4. 5-benzyl-2-(2-hydroxyethylthio)-benzimidazole or a pharmaceutically acceptable acid addition salt thereof as defined in claim 3.

5. A compound of the Formula (Id)

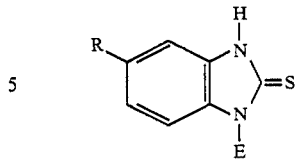

wherein
E is $C_4$ to $C_6$ alkyl substituted by oxo; and
R is $C_4$ to $C_6$ alkyl, phenyl-($C_1$ to $C_4$ alkyl), benzoyl, or phenylsulfinyl, or a pharmaceutically acceptable acid addition salt thereof.

6. 1-(5-benzyl)-2-thioxo-1-benzimidazolyl)-3-butanone or a pharmaceutically acceptable acid addition salt thereof defined in claim 5.

7. A compound of the Formula (Ie)

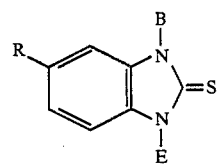

wherein
B and E are each $C_4$ to $C_6$ alkyl substituted by oxo; and
R is $C_1$ to $C_4$ alkyl, phenyl-($C_1$ to $C_4$ alkyl), benzoyl or phenylsulfinyl; or pharmaceutically acceptable acid addition salt thereof.

8. 1,3-bis(3-oxobutyl)-5-benzoyl-2-thioxobenzimidazole or a pharmaceutically acceptable acid addition salt thereof as defined in claim 7.

9. A compound of the Formula (If)

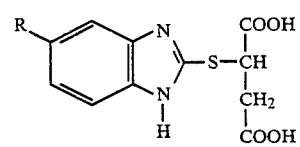

wherein
R is phenyl-($C_1$ to $C_4$ alkyl), benzoyl, or phenylsulfinyl; or a pharmaceutically acceptable acid addition salt thereof.

10. S-(5-benzoyl-2-benzimidazolyl)-2-thio-succinic acid or a pharmaceutically acceptable acid addition salt thereof as defined in claim 9.

11. S-(5-benzyl-2-benzimidazolyl)-2-thio-succinic acid or a pharmaceutically acceptable acid addition salt thereof as defined in claim 9.

12. A compound of the Formula (Ig)

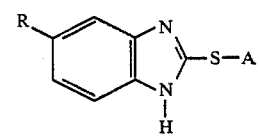

wherein
A is $C_3$ to $C_4$ alkenyl, $C_3$ to $C_4$ alkynyl, or 2-oxo-propyl; and R is $C_1$ to $C_4$ alkyl, phenyl-($C_1$ to $C_4$ alkyl), benzoyl, or phenylsulfinyl, or a pharmaceutically acceptable acid addition salt thereof.

13. 5-methyl-2-(2-propynylthio)-benzimidazole or a pharmaceutically acceptable acid addition salt thereof as defined in claim 12.

14. 5-benzoyl-2-(2-propenylthio)benzimidazole or a pharmaceutically acceptable acid addition salt thereof as defined in claim 12.

15. 1-[(5-benzoyl-2-benzimidazolyl)-thio]-2-propanone or a pharmaceutically acceptable acid addition salt thereof as defined in claim 12.

16. A compound of the Formula (Ih)

[Structure: benzimidazole with R substituent, connected via S—$CH_2$—C(=O)—$CH_2$—C(=O)—O—Et, N-H]

wherein
R is $C_1$ to $C_4$ alkyl, phenyl-($C_1$ to $C_4$ alkyl), benzoyl, or phenylsulfinyl, or a pharmaceutically acceptable acid addition salt thereof.

17. 4-[(5-benzoyl-2-benzimidazolyl)thio]-acetoacetic acid ethyl ester or a pharmaceutically acceptable acid addition salt thereof as defined in claim 16.

18. A compound of the Formula (Ik)

[Structure: benzimidazole with R substituent, 2-S—A, N-H]

wherein
A is methyl, $C_2$ to $C_4$ alkyl unsubstituted or substituted by one or more halogen atoms, oxo, carboxy, hydroxy, hydroxyimino, phenyl, halophenyl, carboalkoxy having 2 to 5 carbon atoms, carbamoyl or nitrile or by —$NR^1R^2$ wherein $R^1$ and $R^2$ independently from each other represent hydrogen or alkyl having 1 to 4 carbon atoms, or $R^1$ and $R^2$ together represent an α,ω-alkylene chain having 4 or 5 carbon atoms optionally interrupted by oxygen; or A is $C_3$ to $C_4$ alkenyl or $C_3$ to $C_4$ alkynyl; and where A is substituted $C_2$ to $C_4$ alkyl, the substituent is bonded to a carbon atom of said alkyl group different from the carbon atoms of said alkyl group bonded to the adjacent sulfur atom; and R is phenyl-($C_1$ to $C_4$ alkyl), benzoyl, or phenylsulfinyl; but where R is benzoyl, A cannot be methyl; or a pharmaceutically acceptable acid addition salt thereof.

19. 5-benzyl-2-(3-hydroxypropylthio)-benzimidazole or a pharmaceutically acceptable acid addition salt thereof as defined in claim 18.

20. A compound of Formula (Il)

[Structure: benzimidazole with two R substituents, 2-S, N—$(CH_2)_n$]

wherein one R is phenyl-($C_1$ to $C_4$ alkyl), benzoyl or phenylsulfinyl, and the other R is hydrogen;
n is 2 or 3; or a pharmaceutically acceptable acid addition salt thereof.

21. A compound of the Formula (Im)

[Structure: benzimidazole with two R substituents, N-B and N-E, =S]

wherein
B and E stand independently of each other for hydrogen or alkyl having 4 to 6 carbon atoms substituted by an oxo or hydroxyimino group in the γ-position, but one B and E must be different from hydrogen;
one R is $C_1$ to $C_4$ alkyl, phenyl-($C_1$ to $C_4$ alkyl), benzoyl, or phenylsulfinyl, and the other R is hydrogen, or a pharmaceutically acceptable acid addition salt thereof.

22. An antihyperlipoproteinemic pharmaceutical composition comprising an antihyperlipoproteinemic effective amount of the compound of the Formula (Im) as defined in claim 21, or a pharmaceutically acceptable acid addition salt thereof, in admixture with a pharmaceutically acceptable inert carrier.

23. A method for treating hyperlipoproteinemic disease which comprises the step of administering to a mammal in need of said treatment, an antihyperlipoproteinemic effective amount of the compound of the Formula (Im) as defined in claim 21, or a pharmaceutically acceptable acid addition salt thereof.

24. A compound of the Formula (Ij)

[Structure: benzimidazole with R substituent, 2-S—$CH_2$—$(CH_2)_n$—N with $R^1$ and $R^2$, N-H]

wherein
$R^1$ and $R^2$ independently from each other represent hydrogen or alkyl having 1 to 4 carbon atoms, or $R^1$ and $R^2$ together represent an α,ω-alkylene chain having 4 or 5 carbon atoms optionally interrupted by oxygen;
R is $C_1$ to $C_5$ alkyl; and
n is 1 or 2; or a pharmaceutically acceptable acid addition salt thereof.

25. An antihyperlipoproteinemic pharmaceutical composition comprising an antihyperlipoproteinemic effective amount of the compound of the Formula (Ij) as defined in claim 24, or a pharmaceutically acceptable acid addition salt thereof, in admixture with a pharmaceutically acceptable inert carrier.

26. A method for treating hyperlipoproteinemic disease which comprises the step of administering to a mammal in need of said treatment, an antihyperlipoproteinemic effective amount of the compound of the Formula (Ij) as defined in claim 24, or a pharmaceutically acceptable acid addition salt thereof.

27. An antihyperlipoproteinemic pharmaceutical composition comprising an antihyperlipoproteinemic effective amount of the compound of the Formula (Ik)

as defined in claim 18, or a pharmaceutically acceptable acid addition salt thereof, in admixture with a pharmaceutically acceptable inert carrier.

28. A method for treating hyperlipoproteinemic disease which comprises the step of administering to a mammal in need of said treatment, an antihyperlipoproteinemic effective amount of the compound of the Formula (Ik) as defined in claim 18, or a pharmaceutically acceptable acid addition salt thereof.

29. An antihyperlipoproteinemic pharmaceutical composition comprising an antihyperlipoproteinemic effective amount of the compound of the Formula (Il) as defined in claim 20, or a pharmaceutically acceptable acid addition salt thereof, in admixture with a pharmaceutically acceptable inert carrier.

30. A method for treating hyperlipoproteinemic disease which comprises the step of administering to a mammal in need of said treatment, an antihyperlopoproteinemic effective amount of the compound of the Formula (Il) as defined in claim 20, or a pharmaceutically acceptable acid addition salt thereof.

* * * * *